(12) United States Patent
Kete

(10) Patent No.: US 8,920,584 B2
(45) Date of Patent: Dec. 30, 2014

(54) MANUFACTURING PROCESS AND A HIGHLY ABSORBENT PAD FOR A CAT LITTER

(75) Inventor: Evgen Kete, Ajdovscina (SI)

(73) Assignee: TT Okroglica d.d. (SI)

( * ) Notice: Subject to any disclaimer, the term of this patent is extended or adjusted under 35 U.S.C. 154(b) by 133 days.

(21) Appl. No.: 13/542,970

(22) Filed: Jul. 6, 2012

(65) Prior Publication Data

US 2013/0174791 A1 Jul. 11, 2013

Related U.S. Application Data

(60) Provisional application No. 61/504,801, filed on Jul. 6, 2011.

(51) Int. Cl.
  *A01K 1/015* (2006.01)
  *B29C 65/20* (2006.01)
  *A01K 1/01* (2006.01)
  *A61F 13/515* (2006.01)
  *B29C 65/00* (2006.01)

(52) U.S. Cl.
  CPC ............. *A01K 1/0154* (2013.01); *A01K 1/0107* (2013.01); *A61F 13/515* (2013.01); *B29C 65/20* (2013.01); *B29C 66/43* (2013.01)
  USPC .......................... 156/62.2; 156/276; 156/308.4

(58) Field of Classification Search
  CPC ... A01K 1/0107; A01K 1/0157; A01K 29/00; A61F 13/515; A61F 13/15577; A61F 13/15634; B29C 65/242; B29C 65/18; B29C 65/20; B29C 66/43; B32B 7/0076

USPC ........... 156/62.2, 276, 290, 292, 308.4, 309.9
See application file for complete search history.

(56) References Cited

U.S. PATENT DOCUMENTS

| 4,014,341 | A | * | 3/1977 | Karami | 604/366 |
| 4,869,204 | A | * | 9/1989 | Yananton | 119/169 |
| 5,797,347 | A | * | 8/1998 | Ochi | 119/169 |
| 5,850,798 | A | * | 12/1998 | Engel | 119/170 |
| 2004/0255869 | A1 | * | 12/2004 | Matsuo et al. | 119/170 |
| 2006/0142709 | A1 | * | 6/2006 | Quincy, III | 604/359 |
| 2009/0044756 | A1 | * | 2/2009 | Otsuji et al. | 119/169 |
| 2011/0146581 | A1 | * | 6/2011 | Sasano et al. | 119/171 |

FOREIGN PATENT DOCUMENTS

WO WO 2010/024308 A1 * 3/2010

* cited by examiner

*Primary Examiner* — Michael Tolin
(74) *Attorney, Agent, or Firm* — The Watson I.P. Group, PLC; Jovan N. Jovanovic; Vladan M. Vasiljevic

(57) ABSTRACT

A manufacturing process and a highly absorbent pad for a cat litter tray, which encourages the transformation of the liquid (feline urine) into a viscous state in the form of a gel and moreover, prevents the appearance of the unpleasant odors in the room and excessive bacterial growth and thus extending the usefulness of sand in a cat litter tray. The highly absorbent pad is composed of wrapped thermoplastic non-woven textiles made of a highly absorbent powder that absorbs moisture. In contact with the liquid, the pad begins to swell. The absorbent powder transforms from the solid state in the viscous state in the form of a gel.

3 Claims, No Drawings

MANUFACTURING PROCESS AND A HIGHLY ABSORBENT PAD FOR A CAT LITTER

CROSS-REFERENCE TO RELATED APPLICATION

This application claims priority from U.S. Prov. Pat. App. Ser. No. 61/504,801 filed Jul. 6, 2011, entitled Manufacturing Process and a Highly Absorbent Pad for a Cat Litter Tray.

BACKGROUND

The subject of the invention is the manufacturing process of a highly absorbent pad for a cat litter tray which allows a transformation of the liquid (feline urine) into a viscous state in the form of a gel and moreover, prevents unpleasant odours in the room and excessive bacterial growth and thereby extending the usefulness of sand for a cat litter tray. The invention belongs to a class A 01 K 29/00.

The invention represents a successful solution for the technical problem as it defines the process of manufacture and use of the pad for a cat litter tray which extends the usefulness of sand for a cat litter tray while preventing the appearance of the unpleasant odours and a possibility of bacterial growth.

There is in a container of a cat litter tray, which is now mostly used, a material, i.e. a specific type of "sand" which contains mainly high absorbent materials with disinfectant elements and possibly the components to prevent the appearance of the unpleasant odours. For example, the patent document RO 121885 determines a composition of a mixture for a cat litter tray of dry material obtained from moulds of a ceramic industry as pottery plaster and kaolin clay and also of neutralizing material in the form of sodium hydrogen and disinfectant element in the form of urea peroxide. The patent document WO2004010772 represents a granular mixture containing herbal products based on cellulose and acid pyrophosphate salts with alkaline earth metal. There are sat horn tree trunks as vegetable products based on cellulose and sodium as a salt of acid pyrophosphate. The combination has a high capacity of absorption, is environmentally friendly and may be removable.

The effective components for absorption and disinfection are of key importance for the composition of the "sand" for a cat litter tray described above. Nevertheless, there still remains to improve effectively the capacity of absorption in the amount as dictated by the size of a container of a cat litter tray. There is a possibility to achieve a higher level of absorption capacity for a longer period. Therefore, the actual filling has to be changed in a shorter period of time, which consequently requires more financial means.

There are also cat litter trays with layers at the bottom of a container, one of which allows the absorption of fluids and the other is infiltrated by the components that enable disinfection and taking effect of a deodorant. Both layers are covered with sand; mainly for the purpose of facilitating the movement of an animal that is to say to prevent the damages on the layer of absorbent made by the animal's claws. The layers can be removed and discarded after a time. Such solution is described in the U.S. Pat. Nos. 4,869,204 and 4,800,841.

The main disadvantage of the mentioned solution is a limited use of a particular layer adapted to each container in such manner to allow a fixation of a layer. The usefulness of a thinner layer is of a shorter time which requires frequent replacement.

The invention provides a solution for the technical aspect of the problem by the means of the manufacturing process and a highly absorbent pad for a cat litter tray which is intended to be placed under the sand in a cat litter tray. The pad consists of a layer of thermoplastic non-woven textiles and powder components which have the capacity to be transformed in a contact with the liquid (feline urine) from the solid to the viscous state in the form of a gel.

The invention is presented in details afterwards the description of the manufacturing process of a highly absorbent pad for a cat litter tray and the composition of a highly absorbent pad.

According to the invention a highly absorbing pad is composed of wrapped thermoplastic non-woven textiles made of a highly absorbent powder that absorbs moisture. In contact with the fluid the pad begins to swell. It is the absorbent powder that changes from the solid in the viscous state in the form of a gel.

DETAILED DESCRIPTION

The process of manufacture of a highly absorbent pad is composed one phase. The upper and lower thermoplastic component are jointed together with the phase of the process, namely the coating stage-application of grit on various textile and technical materials carried out by the machine. The lower thermoplastic non-woven textiles treated with a carbon paste go to the area where undertaking the application of a highly absorbent grit and fragrance neutralisation. Non-woven textiles sprinkled with a mixture of a highly absorbent powder travel through the heat chamber where prepared for bonding with the upper wrapping layer of non-woven textiles. From the other unrolling device comes a non-woven material treated with an antibacterial aperture covering the material and sprinkled with a mixture of a highly absorbent powder. Both materials go to two compression cylinders which merge them into a pad.

The next stage is welding of the pad—according to its width dimension—to a particular dimension that is suitable for a cat litter tray. By means of heath and pressure the edges of a pad are melted. Thereby, leakage of gel is prevented.

A highly absorbent pad for a cat litter tray is an invention that offers a perfect solution for the technical problem since by the means of the pad the usefulness of a standard "sand" is longer. In addition, it reduces the appearance of the unpleasant odours of feline urine, absorbs urine, is simple to use and maintain, reduces consumption of "sand" and makes it easier to clean a cat litter tray, prolongs its usefulness and prevents sticking of sand to the bottom of a cat litter tray. The pad has a high capacity of retention of fluid since the level of absorption of a pad with dimensions of 24×34 cm is approx 1.7 liters.

The invention claimed is:

1. Manufacturing process of a highly absorbent pad for a cat litter tray comprising the following steps:
   providing an upper and a lower thermoplastic non-woven textile, the upper thermoplastic non-woven textile including apertures;
   sprinkling a mixture of a highly absorbent powder on the lower thermoplastic non-woven textile;
   treating the upper thermoplastic non-woven textile including apertures with an antibacterial material;
   sprinkling a mixture of a highly absorbent powder on the upper thermoplastic non-woven textile;
   passing the upper and lower thermoplastic non-woven textiles through a heat chamber;
   merging the upper and lower thermoplastic non-woven textiles between two compression cylinders into a pad;
   welding the pad to a particular dimension that is suitable for a cat litter tray, wherein the step of welding further includes the step of melting each corresponding edge of the upper and the lower thermoplastic non-woven textiles means of heat and pressure.

2. The process according to the claim 1, wherein in the highly absorbent powder sprinkled on the thermoplastic non-woven textiles comprises a powder which upon contact with liquid transforms from a solid to a gel.

3. The process according to the claim 1, wherein the upper and lower thermoplastic non-woven textiles each comprise a hot melt ethylene vinyl acetate and the highly absorbent powder comprises a polycarbonate powder.

* * * * *